United States Patent
Mueller et al.

(10) Patent No.: US 8,932,544 B2
(45) Date of Patent: Jan. 13, 2015

(54) MICROREACTOR ARRAY, DEVICE COMPRISING A MICROREACTOR ARRAY, AND METHOD FOR USING A MICROREACTOR ARRAY

(75) Inventors: Carsten Mueller, Aachen (DE); Ingo Klammer, Aachen (DE); Frank Kensy, Aachen (DE); Jochen Buechs, Aachen (DE); Mirko Hofmann, Reutlingen (DE); Andreas Buchenauer, Aachen (DE); Uwe Schnakenberg, Aachen (DE); Wilfried Mokwa, Aachen (DE)

(73) Assignee: m2p-labs GmbH, Aachen (DE)

( * ) Notice: Subject to any disclaimer, the term of this patent is extended or adjusted under 35 U.S.C. 154(b) by 518 days.

(21) Appl. No.: 12/308,837

(22) PCT Filed: Jun. 28, 2007

(86) PCT No.: PCT/DE2007/001143
§ 371 (c)(1),
(2), (4) Date: Jan. 13, 2009

(87) PCT Pub. No.: WO2008/000238
PCT Pub. Date: Jan. 3, 2008

(65) Prior Publication Data
US 2009/0320622 A1    Dec. 31, 2009

(30) Foreign Application Priority Data
Jun. 28, 2006   (DE) .................. 10 2006 030 068

(51) Int. Cl.
*B01L 3/00*    (2006.01)
*B01J 8/00*    (2006.01)
*B06B 1/00*    (2006.01)
*C12M 3/06*    (2006.01)
*B01J 19/00*   (2006.01)
*C12M 1/32*    (2006.01)

(52) U.S. Cl.
CPC .. *B01L 3/502738* (2013.01); *B01J 2219/00891* (2013.01); *B01L 2200/0642* (2013.01); *B01L 2400/06* (2013.01); *B01L 2300/047* (2013.01);
(Continued)

(58) Field of Classification Search
None
See application file for complete search history.

(56) References Cited

U.S. PATENT DOCUMENTS 6,202,713 B1   3/2001   Drescher et al.
6,268,219 B1   7/2001   Mcbride et al.
(Continued)

FOREIGN PATENT DOCUMENTS

DE   100 19 862   11/2001
DE   100 41 853   2/2002
(Continued)

OTHER PUBLICATIONS

C.H. Mastrangelo et al., Microfabricated devices for genetic diagnostics, 1998, Proc. of the IEEE 86(8): 1769-1787.*
(Continued)

*Primary Examiner* — Jill Warden
*Assistant Examiner* — Timothy G Kingan
(74) *Attorney, Agent, or Firm* — Collard & Roe, P.C.

(57) ABSTRACT

Disclosed are a method and a device for feeding and/or discharging fluids in microreactor arrays through one or several fluid ducts that extend into each individual microreactor and can be individually controlled and regulated, in order to control, regulate, influence, and/or verify processes. The fed or discharged amounts of fluid are introduced into or discharged from the volume of the reaction liquid during a continuous shaking process and are evenly mixed as a result of the shaking process. The continuous shaking process causes sufficient mass transfer and thorough mixing of the reaction partners or fluids while the reaction is not limited or restricted by the mass transfer conditions.

26 Claims, 9 Drawing Sheets

(52) U.S. Cl.
CPC .. *B01L 2200/0605* (2013.01); *B01L 2300/0861* (2013.01); *B01L 2300/0829* (2013.01); *B01L 2400/0688* (2013.01); *C12M 23/16* (2013.01); *B01L 2400/021* (2013.01); *B01L 2400/022* (2013.01); *B01L 2400/0655* (2013.01); *B01L 2400/043* (2013.01); *B01L 2400/0481* (2013.01); *B01L 2400/0415* (2013.01); *B01L 2400/0454* (2013.01); *B01L 3/502715* (2013.01); *B01J 19/0093* (2013.01); *B01L 3/5025* (2013.01); *B01L 2300/0819* (2013.01); *B01L 2300/10* (2013.01); *B01L 2300/0867* (2013.01); *B01L 3/50273* (2013.01); *C12M 23/12* (2013.01); *B01L 2400/0442* (2013.01); *B01L 2400/0439* (2013.01); *C12M 27/16* (2013.01); *B01L 2400/0661* (2013.01)
USPC ........... 422/603; 422/128; 422/129; 422/209; 422/224; 422/552; 422/559; 422/600; 422/602; 435/286.5; 435/286.6; 435/286.7; 435/287.8; 435/288.2; 435/288.5

(56) References Cited

U.S. PATENT DOCUMENTS

| | | | |
|---|---|---|---|
| 6,284,113 B1 * | 9/2001 | Bjornson et al. ............. 204/453 |
| 6,403,338 B1 | 6/2002 | Knapp et al. |
| 6,599,736 B2 | 7/2003 | McCaskill et al. |
| 6,908,767 B2 | 6/2005 | Bader |
| 7,156,118 B2 | 1/2007 | Ocvirk et al. |
| 7,794,668 B2 * | 9/2010 | Bar et al. .................... 422/129 |
| 2003/0008308 A1 | 1/2003 | Enzelberger et al. |
| 2003/0012657 A1 | 1/2003 | Marr et al. |
| 2003/0064507 A1 | 4/2003 | Gallagher et al. |
| 2003/0157701 A1 * | 8/2003 | Sollboehmer et al. ..... 435/288.4 |
| 2004/0115731 A1 | 6/2004 | Hansen et al. |
| 2004/0189311 A1 * | 9/2004 | Glezer et al. ................. 324/444 |
| 2005/0003421 A1 * | 1/2005 | Besemer et al. ................. 435/6 |
| 2005/0032204 A1 | 2/2005 | Rodgers et al. |
| 2005/0047967 A1 | 3/2005 | Chuang et al. |
| 2005/0084421 A1 | 4/2005 | Unger et al. |
| 2005/0084923 A1 | 4/2005 | Mueller et al. |
| 2005/0089993 A1 * | 4/2005 | Boccazzi et al. ........... 435/286.2 |
| 2005/0129581 A1 * | 6/2005 | McBride et al. .............. 422/100 |
| 2005/0133713 A1 * | 6/2005 | Brennen ....................... 250/288 |
| 2005/0142664 A1 | 6/2005 | Loney |
| 2005/0233198 A1 * | 10/2005 | Nuzzo et al. .................... 429/34 |
| 2006/0260713 A1 * | 11/2006 | Pyszczek et al. ......... 141/311 R |
| 2007/0009382 A1 * | 1/2007 | Bedingham et al. ............ 422/63 |

FOREIGN PATENT DOCUMENTS

| | | | |
|---|---|---|---|
| DE | 100 46 175 | 3/2002 |
| DE | 600 00 109 | 11/2002 |
| DE | 101 16 642 | 12/2002 |
| DE | 102 01 749 | 8/2003 |
| DE | 102 21 565 | 12/2003 |
| DE | 102 54 564 | 12/2003 |
| DE | 10221565 | * 12/2003 | ............... C12M 1/18 |
| DE | 102 38 825 | 3/2004 |
| DE | 103 29 820 | 1/2005 |
| EP | 1 036 594 | 9/2000 |
| EP | 1 142 641 | 10/2001 |
| EP | 1 065 378 | 4/2002 |
| EP | 1 415 710 | 5/2004 |
| WO | WO 01/68257 | 9/2001 |
| WO | WO 02/37096 | 5/2002 |
| WO | WO 02/060582 | 8/2002 |
| WO | WO 02/080822 | 10/2002 |
| WO | WO 03/025113 | 3/2003 |
| WO | 03/103813 A2 | 12/2003 |
| WO | 2004/016727 A1 | 2/2004 |
| WO | WO 2004/069983 | 8/2004 |

OTHER PUBLICATIONS

European Office Action for 07 785 576.5-1356 dated May 28, 2013 with English Translation.

* cited by examiner

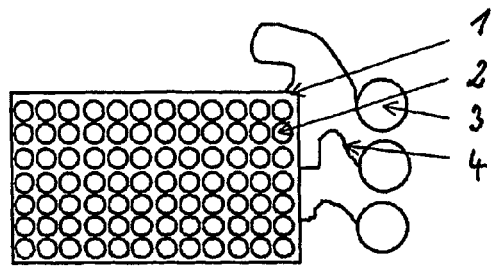
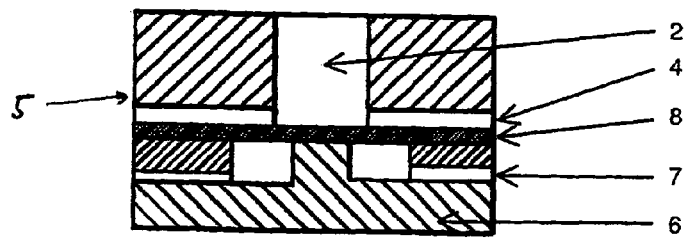
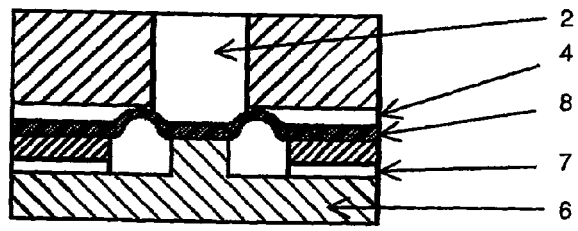
Fig. 2
Fig. 3
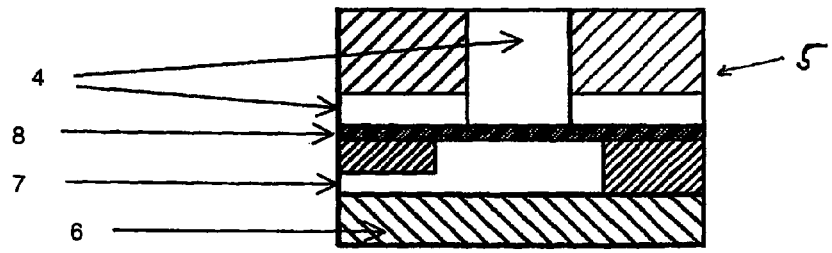
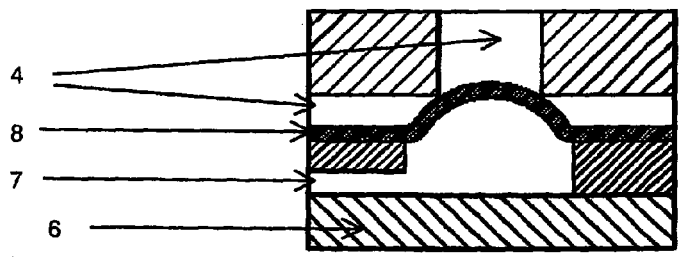
Fig. 4

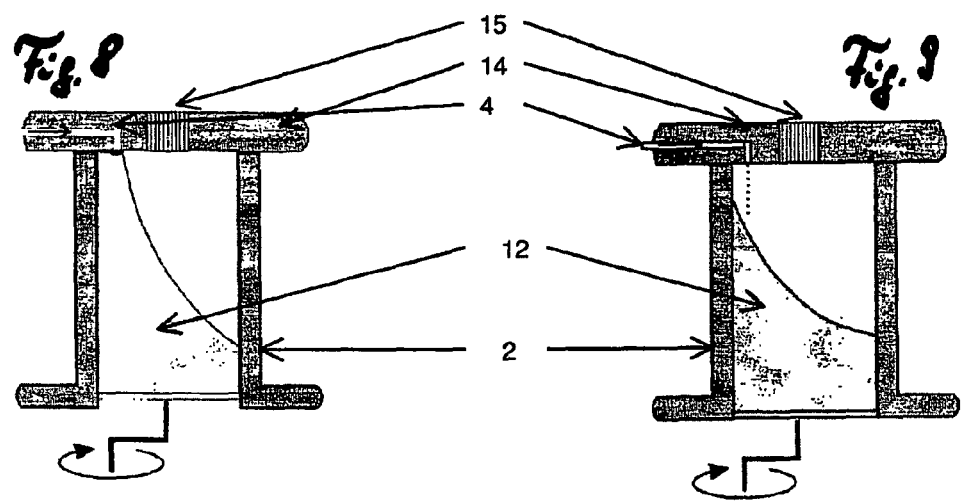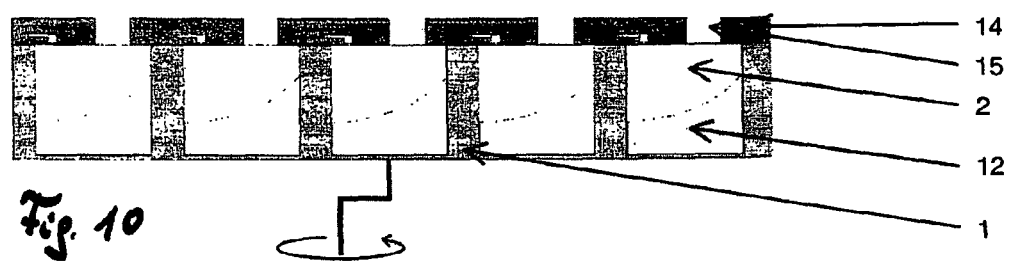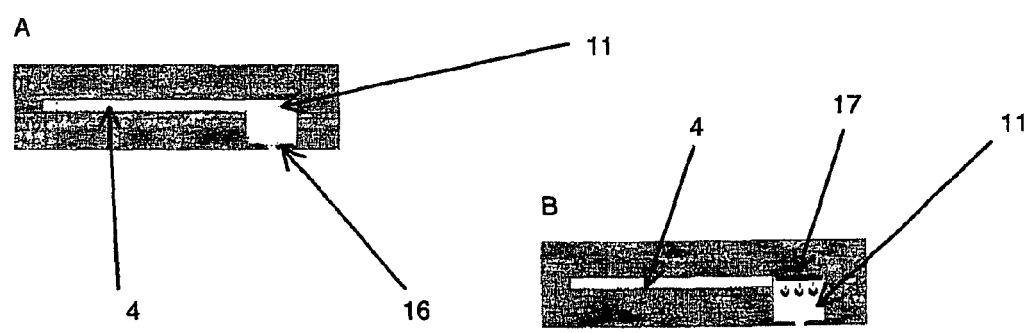

MICROREACTOR ARRAY, DEVICE COMPRISING A MICROREACTOR ARRAY, AND METHOD FOR USING A MICROREACTOR ARRAY

CROSS REFERENCE TO RELATED APPLICATIONS

This application is the National Stage of PCT/DE2007/001143 filed on Jun. 28, 2007, which claims priority under 35 U.S.C. §119 of German Application No. 10 2006 030 068.8 filed on Jun. 28, 2006. The international application under PCT article 21(2) was not published in English.

BACKGROUND

The invention relates to a microreactor array, a device comprising a microreactor array, and a method for using a microreactor array. By means, of conventional titer plates it becomes possible to implement microreactor arrays of, for example, 6, 24, 48, 96, 384 or more individual microreactors. Just as the number of microreactors varies greatly, so can the volume of the individual reactors. While the term "microreactors" is used already at scales of below 10 ml, further reduction of the volume to below 1 ml, below 500 µl, below 100 µl or even below 10 µl can be associated with some advantages. The surface-to-volume ratio that has been increased by the volume reduction is larger, and oxygen input into the reaction solution through simple diffusion is simpler. The microreactor arrays can be shaken continuously until the end of the reaction. Individual metered addition makes it possible to carry out various experiments in each individual reactor. The invention is, in particular, also suitable for automating screening experiments in a fedbatch mode, a continuous mode and/or pH regulation. The invention relates in particular to microbial, biochemical, enzymatic and chemical reactions. The invention supports sterile, aseptic or monoseptic operation.

Process parameters such as for example the pH value, concentrations of dissolved oxygen, dissolved carbon dioxide, biomass, educt and product, or temperature can be used as controller outputs for controlling the metered addition. Particularly suitable, in the context of the invention, is a non-invasive acquisition of the process parameters with the use of optical or electromagnetic measuring methods through the bottom that is permeable to electromagnetic radiation.

In many areas of biology, process technology, pharmacy and medicine, screening of biological systems becomes necessary (e.g. selection of suitable biological strains, enzymes or suitable culture media and culture conditions). In this context there is a need for high sample throughputs (parallelisation of the experiments) and for a reduction in the quantity of reactants, some of which are expensive.

By means of the bioreactors in use at present, for example shaker flasks, small-scale fermenters and test tubes, it is not possible to meet this demand. Established techniques do not meet the requirements for automation, cost minimisation and the required high throughput. In particular in the case of biocatalytic systems, there is a requirement to carry out many parallel experiments at the microliter scale, because such processes, generally speaking, progress more slowly and especially in the development phase are more expensive than comparable chemical processes. It is therefore necessary to develop microbioreactors that in the smallest possible space provide a suitable environment for biological cultivation and biocatalytic reactions. In this context two criteria should be underlined as being important prerequisites for suitable operating conditions: the possibility of carrying out the corresponding experiments under sterile or monoseptic conditions, and ensuring mass transfer (liquid-liquid; liquid-gas; solid-liquid; solid-gas) that is suitable and adequate for the biological culture or for the biocatalytic reaction system.

Microreactor arrays, for example microtiter plates (MTPs) provide an ideal platform in order to achieve a high number of parallel operations. Due to the small reaction volumes (e.g. <10 µL to >5 mL per chamber), the high number of parallel operations (e.g. 6 to 1536 chambers per plate) and the option of automating the cultivation processes (in a form that can be handled by robots), microreactor arrays represent the bioreactor that overall is most cost-effective and that has the most promising future. Furthermore, the use of non-invasive optical measuring methods in order to acquire process variables is already quite advanced in this reactor type. Moreover, the operating conditions in shaken MTPs as far as the mass transfer (maximum oxygen transfer capacity) is concerned are already well characterised (Hermann et al., 2002) and are thus comparable to the operating conditions in laboratory reactors, pilot reactors or production reactors.

For these very reasons there has recently been an increase in the use of microreactor arrays. At present, microtiter plates are already used for screening biological systems. To this effect the individual reaction chambers are filled, inoculated, and incubated on a rotary shaker. As a result of the shaking movement the feed of oxygen into the reaction fluids is improved, and thorough mixing of the reaction fluids is achieved. Apart from the shaking movement there are other possible options that may be considered for thoroughly mixing fluids in microtiter plates (e.g. moving the fluid by means of sound waves). In order to keep the system sterile, the microtiter plates are covered by an air-permeable membrane (pore size <0.2 µm) or airproof film or foil or a cover construction, or cultivation takes place in an open manner in a sterile environment.

In order to carry out the different biocatalytic reactions it is often necessary to add to the ongoing reaction various fluids or gasses while the experiment is ongoing. In this context the supply of pH adjusters (alkaline solutions and acids) for pH titration of the ongoing reaction, and the infeed of substrates should be emphasized. It is only the infeed of substrates during the process that makes it possible to carry out regulated batch, fedbatch and continuous processes. These modes of operation are particularly important for flexible and successful biological screening and for further development of the processes.

A brief discussion of the importance of the most important operating methods is provided below.

The pH value of a medium is one of the most important environmental influences for cell growth and for the ability of micro-organisms to develop. The activities of the enzymes that catalyse all the reactions due to the metabolic process are decisively influenced by the pH value. However, the pH value of the medium continuously changes as a result of the metabolism of the organisms and as a result of the consumption of the components of the culture medium. If pH regulation is lacking, it is difficult to achieve high cell densities. Therefore regulation of the pH value by titration of pH adjusters (alkaline solution or acid) is necessary. The pH adjuster can be in liquid or gaseous form.

In industrial production processes the fedbatch mode (cultivation with the infeed of substrate) is the standard process. The fedbatch mode is necessary in many production processes, for example in order to prevent inhibition as a result of excessive substrate concentrations or catabolite repression. Fedbatch mode must therefore be possible for the corresponding bioreactors. In addition it is precisely in this mode, where the pH value changes greatly, that pH regulation is almost always necessary.

Furthermore, continuous reaction management of biocatalytic systems is important in order to achieve a steady state or steady-state balance and in order to determine kinetic parameters, as well as to carry out long-term experiments (e.g. to determine the genetic stability of genetically modified microorganisms).

For many decades, regulating the pH value and carrying out the reactions in fedbatch mode has been the state of the art in large-scale industrial applications. Likewise, commercially available small-scale (>10 mL-500 mL) reactor systems are becoming increasingly widespread (e.g. fedbatch pro by DasGip [U.S. Pat. No. 6,202,713], Sixfors by Infors, etc.).

Small-scale reactor systems are used for screening and process development; they can be operated under the above-mentioned conditions. However, the following applies: the smaller the reaction volume, the more elaborate and cost-intensive the implemented solution. Due to the very considerable technical expenditure in the case of small reaction volumes, and due to the low achievable degree of parallel operation in the case of greater reaction volumes, the proposed approaches to this problem are associated with very considerable limitations. For example, in the current approaches it is not possible to have high-throughput screening (>16, >20, >50, >500, >1,000, >10,000 to >100,000 reactions per day) while at the same time providing high-content screening (>1, >2, >3, >4, >5 reaction parameters for each reaction point in time). At present different approaches to finding a solution have been implemented or are pursued to implement the described operational modes in microreactor arrays. Broadly-speaking, a differentiation can be made among contactless, contacting, and microfluidic dosing methods.

The technique for contactless metered addition of very small quantities of fluid is largely based on piezo technology. As a result of the very considerable instances of acceleration (up to 100,000 g) that can be achieved by a piezo element, it is possible to separate, and thus to dose, very small droplets (>30 pL) from a reservoir. Various companies (e.g. Nano-Plotter™ by GeSim; Autodrop by Microdrop) market devices for the metered addition of very small volumes of fluid in MTPs.

Furthermore, contactless dosing methods exist that are operated with the use of compressed air (e.g. Vieweg GmbH) [EP 1036594]. The achievable droplet volumes range from approximately 5 µL to 0.2 mL. Furthermore, there are patents relating to the cultivation of cells in microreactors with the use of droplet infeed of reaction fluids [DE 10221565, DE 10019862, DE 10046175]. In these approaches the reaction fluids are fed through capillaries to the reaction chamber or above the reaction chamber until at the tip of the capillary a droplet of adequate size has formed, which droplet then drips into the reaction space. In the case of aqueous media the volume of such a droplet is in the order of approximately 20 µL, depending on the diameter and the design of the needles.

In contacting dosing methods the infeed of fluids mostly takes place by controlled dipping of pipette tips into the reaction fluids of the individual chambers of the microreactor arrays by way of a pipetting robot. In this process serially (one pipette tip) or in parallel (several pipette tips) the desired quantities of fluids are metered to the individual chambers. By dipping the pipette into the reaction fluid the metered droplet can be separated from the pipette tip so that quantities in the picoliter range can also be dosed [DE 10201749, DE10116642, WO 02/080822].

Utilisation of microfluidic transport in microreactors is not new either. There are already several approaches for transporting and controlling minute quantities of fluid in microreactors, e.g. WO 02/37096, U.S. Pat. No. 6,403,338, EP 1142641, DE 60000109, U.S. Pat. No. 6,268,219, WO 01/68257, US 2005/0032204; US 2005/0084421, WO 02/060582, WO 03/025113, WO01/68257, WO2004/069983.

Taking into consideration the current approaches and evaluation of them by applying the criteria of sterile operation of the reaction space, oxygen supply of the biological cultures, and realisation of individual infeed and discharge of fluids, the individual approaches are associated with the following disadvantages.

While contactless jet-dosing based on piezo technology makes it possible to dose very small quantities of fluid, these methods are however cost-intensive and prone to malfunction.

When compared to piezo-technology-based methods, pressure-driven or gravity-driven methods are more cost-effective, but they are associated with a disadvantage in that only comparatively larger droplet volumes (>5 µl or <0.2 mL) can be dosed. As a result of the volume ratio of the infed droplets to the reaction volume of the individual microtiter plates, at the time of adding a droplet of reaction fluid an extreme increase in the corresponding concentrations in the reaction chambers takes place. As a result of these extreme concentration increases the experiments are considerably influenced so that the analysis results obtained are not representative and cannot be transposed to larger scales. Such extreme increases in concentration can then only be counteracted by an increase in the volume of the culture.

Contactless dosing methods are associated with a further disadvantage in that closing off the microreactor arrays by means of a membrane or a cover is either not possible at all or is possible only with very considerable expenditure. Closing them is necessary in order to keep the individual reaction vessels of an MTP sterile or monoseptic, and in order to minimise any evaporation of reaction fluid.

Furthermore, contactless dosing methods do not allow dosing during continuous shaking of microreactor arrays. Only intermittent dosing is possible, because any metered addition is only possible after the shaking process has been stopped. However, in the case of biocatalytic reactions non-intermittent metered addition is desirable because as a result of stopping the shaking movement the operating conditions (e.g. interruption of the oxygen infeed and of thorough mixing) undergo a sudden change, and thus any analysis results obtained in this manner can be used only to a limited extent.

In the case of contacting dosing methods there is a considerable danger of contamination or cross contamination as a result of the pipette dipping into the reaction fluid. Furthermore, with this method, too, closing the microreactor arrays off by means of a membrane or a cover is prevented, and any metered addition of fluids during the shaking process is likewise not possible.

Existing microfluidic approaches relating to the transport and control of minute quantities of fluid in microreactors comprise at least one of the following deficiencies: The methods are not designed to dose variable volumes to individual chambers of microreactor arrays. The methods are exclusively used for the analysis of substances and substance flows, for the separation of substance flows and/or for the preparation of the smallest possible sample volumes. The methods only support even separation of fluid volumes in microreactor arrays. With these methods it is not possible to achieve any targeted metered addition to individual chambers. The methods do not allow any sterile closing off of the microreactor arrays by means of a membrane or a cover. The methods do not support the metered addition or discharge of fluids during continuous shaking of the microreactor arrays in order to thoroughly mix the reaction fluids and in order to set adequate mass transfer rates.

In summary it can be stated that none of the approaches mentioned above make it possible to unify the following requirements of a biotechnological, biochemical or chemical process:
1. individual infeed and discharge of fluids into and from the individual reaction chambers of a microreactor array (e.g. in order to implement pH titration or a fedbatch process);
2. sterile or monoseptic closing-off of the microreactor array during infeed or discharge of fluids;
3. adequate and controlled mass transfer (e.g. for the supply of oxygen) by means of shaking.

SUMMARY

Based on this state of the art it is the object of the invention to remove some of these limitations for microreactor arrays. For, already at the smallest scale of primary screening the operating conditions should be as similar as possible to those of subsequent production, because otherwise selection would take place according to incorrect criteria. An incorrect selection of catalysts (strains, enzymes, proteins or chemical catalysts) in primary screening due to unsuitable test conditions has an effect on the entire subsequent process development and as a rule can no longer be compensated for. The economic disadvantages are likely to be considerable, but they cannot be quantified because up to now no suitable techniques were available at the microscale that would, for example, make possible pH control and fedbatch operation in primary screening.

In order to implement such operating methods in microreactor arrays, due to the small reaction volumes, feeding and discharging the fluid quantities needs to take place in the nano- or picoliter range. This is necessary in order to appropriately influence or regulate the processes and in order to, if necessary, achieve the same ratios of fed-in or discharged volumes to reaction volumes as is the case in larger reactors. In this way scale-up of the results of the analysis can be made possible.

The object is met by a microreactor array comprising several containers and at least one duct that forms a fluid line to the container.

The microreactor array according to the invention supports a fluid system for the infeed and discharge of fluids. A fluid system is defined as a device comprising a duct system that provides various ducts on one plane or on several planes, through which ducts the desired fluids are conveyed. Furthermore, the fluid system preferably comprises valves that can close off the individual ducts, thus allowing control of the fluid ducts. If the ducts for conveying fluid and if the actuators or control devices for the valves are implemented on different planes or substrates, these planes are referred to as control planes. Through the fluid ducts the fluids are individually conveyed to the individual reaction chambers. By means of a concurrent shaking process of the microreactor array, the fluid quantities conveyed to the reaction chambers can mix with the remaining reaction volumes. By means of controlling the individual inflows to the various reaction chambers of the microreactor array, individual inflow and outflow can be implemented.

Controlling the individual fluid ducts can be implemented by various methods. Among other solutions, pneumatic control ducts are imaginable which extend at right angles to the fluid ducts on a different plane and which when subjected to pressure can squeeze and close off the desired fluid duct by means of a thin membrane. However, optically, thermally, electromechanically or magnetically actuated microvalves can be used for controlling the fluid ducts. In order to minimise any diffusion of the reaction media within the reactor, back into the fluid ducts, simple passive valves can be implemented at the inlet of the duct into the reactor.

In addition, the fluid ducts and reactor chambers can be designed such that they are at least partly permeable to electromagnetic radiation (for example light). In this way electromagnetic or non-invasive optical reaction monitoring is made possible. Depending on the measuring task at hand, the fluid system can be designed as the lid, the bottom or the mid-plane of the microreactor array so that access to the microreactors is provided from the top or from the bottom.

In its various embodiments the invention provides the following advantages when compared to hitherto-implemented approaches:

Individual feed and discharge of reaction fluids to and from the individual chambers of the microreactor arrays is made possible.

The feed and discharge of reaction fluids can be implemented such that optical access to each individual chamber of the microreactor array remains ensured. In this way the operating states can be determined in a non-invasive manner in each individual chamber by optical measurements.

Individual metered addition and data acquisition can make it possible to regulate controller outputs for each individual reaction chamber.

Metered addition can take place without the need to interrupt the shaking process.

The reaction chambers can be closed off with a gas-permeable membrane or a gas-permeable cover. This makes possible sterile operation and minimises evaporation, as a result of which the reaction volume can be kept largely constant.

When compared to the state of the art, the arrangement according to the invention and improvements to this arrangement overcome the following disadvantages:

The very small quantities (>10 μL) of fluids (e.g. pH adjusters, substrate) that are required in the individual reaction chambers can be fed to and discharged from the individual chambers in a sterile manner.

The reaction chambers can be closed off in a sterile manner by a semi-permeable membrane or a cover.

Adding the fluids can take place without the need to interrupt any shaking process. The supply of oxygen to the organisms contained in the chambers is thus not interrupted, and continuous thorough mixing of the fluids, solids and gases is ensured.

In relation to its form and applicability, the system can be based on commercially available microtiter plates.

The methods and devices described in the claims disclose further combinations of features that per se are significant in the context of the invention and that also in any further combination among themselves and also in connection with previously-mentioned features describe aspects that are significant in the context of the invention.

It is advantageous if in the microreactor arrays each container comprises a duct. In this way the different containers can receive their supplies individually. In particular for feeding and discharging fluid it can be advantageous if the containers are connected by means of at least two ducts.

This results in a microreactor array in which one or several fluid ducts leads/lead to each individual microreactor. Consequently, the microreactor array can be individually controlled and/or regulated. This makes it possible to provide process management, process regulation, process influencing and/or process control.

An exemplary embodiment provides for the containers to be arranged in one plane, and for the duct to be arranged in the plane of the containers. To this effect the duct can, for example, be implemented in the sidewalls of the microreactor array. The fluids to be dosed are consequently no longer in constant contact with the fluid in the microreactors. In this arrangement, as a result of the fluid crescent generated by shaking, the droplet presented through the fluid duct is separated from the sidewall and is taken up by the reaction fluid.

Another embodiment variant provides for the containers to be arranged in one plane, and for the duct to be arranged underneath the plane of the containers.

In particular if the microreactor array comprises a cover, it is advantageous if the containers are arranged in one plane and if the duct is arranged above the plane of the containers. In this way the fluid ducts can be implemented in the cover of the microreactor array, and the fluids to be dosed are consequently in permanent contact with the fluid in the microreactors. In this embodiment, too, the droplet presented through the fluid duct is removed from the cover as a result of the fluid crescent that is generated by the shaking movement and that extends to the cover, and is taken up by the reaction fluid.

The microreactor array can also be designed such that the fluid ducts for the infeed of fluids are implemented in the cover of the microreactor array, and such that the exits of the fluid ducts do not establish contact with the fluid in the microreactors. The fluid droplets are then removed as a result of considerable acceleration, and are fed to the reaction fluid.

It is understood that various ducts can also be arranged in different positions relative to the plane of the containers.

In order to implement different microreactor arrays it is thus advantageously proposed that the transition between the duct and the container be arranged above the fill plane of the container, and that the array comprises a cover in which the duct is arranged.

It is advantageous if the microreactor array comprises a valve and/or a pump. A valve makes possible the controlled supply of fluids, while a pump provides the necessary increase in pressure in order to convey fluids into the reaction chambers. The exemplary embodiments shown explain that a valve can also be further developed in a simple manner so that it becomes a pump.

In order to control the valve or a pump, a focused light beam, thermal control or control by way of microwaves is proposed. A light beam can also be focused on or guided to the respective valves by way of wave guides which, in particular, are integrated in the control plane. Thermal excitation can, for example, be implemented by means of an electrical heating coil. Further options involve magnetically or inductively controlled valves and pumps.

Furthermore, by way of transitions of hydrophilic and hydrophobic surfaces the duct can assume a valve function. This results in passive valves for controlling the fluids.

It is proposed that the duct comprises thermally or electrically shape-changing materials. Thermally shape-changing polymers and/or metal alloys can be used for this purpose. Furthermore, shape memory alloys (SMAs) and shape memory polymers or electrically shape-changing ceramics (piezo crystals) can be used in the implementation of valves and pumps.

One embodiment provides for the duct to comprise a wall as a valve or pump, which wall is deformable by pressure. As a result of controlled pneumatic or mechanical pressure from the outside, one of the sides of the fluid duct can be pushed into said fluid duct in order to close it off, thus implementing an active valve function or a pump function.

The valves or pumps used in the fluid system can also comprise a film or foil, or a thin substrate that interacts with an electrical circuit that is used as a control plane of the fluid system.

One embodiment provides for indentations on the array to be designed as pneumatic connections. Such indentations and preferably one or several reaction chambers, in particular of a microtiter plate, can be used on a microreactor array as pneumatic connections for controlling the fluid flows.

In particular if pressure is applied to a deformable wall, in the case of a multiple series connection a peristaltic pumping effect can be generated, wherein the pressure acting onto one side of the fluid duct can be generated pneumatically or mechanically.

In particular if the fluid ducts are implemented in the bottom of the microreactor array, the fluids to be dosed, separated by a valve, can be in contact with the reaction fluid in the microreactors. An alternative provides for the fluids to be dosed to be separated from the reaction fluid in the microreactors by means of a partially permeable membrane. To this effect a partially permeable membrane is arranged in the duct or in the container.

It is advantageous if at least one surface of the array is designed to provide optical access. With the use of suitable materials at least one surface of the individual microreactors as an optical access can make possible the individual acquisition of data from the individual microreactors, which data can be used for controlling the processes.

Furthermore, it is advantageous if the microreactor array comprises sensors, in the individual containers, for the acquisition of data. In this arrangement, different sensors, and in particular also chemical sensors in dissolved or immobilised form, can be used, in the individual microreactors, for the individual acquisition of data.

One exemplary embodiment provides for containers of the microreactor array to comprise a form or surface structure that is suitable for minimising any contact between the fluid and the duct. As a result of a special form of the individual microreactors, or additional structures contained in them, minimising the contact between the fluid crescent and the exit of the fluid duct, diffusion of the fluid into the ducts can be prevented.

The object on which the invention is based is also met by a device comprising a microreactor array, which device comprises a movement device. Such a movement device can be a mechanical shaker, a stirrer or an ultrasound device.

It is advantageous if the movement device drives at least one pump that is integrated in the microreactor array. Such a pump can increase the pressure in a fluid duct, which pressure ensures conveyance of the fluid after a valve has been opened.

One embodiment provides for the duct to be designed and to be arranged relative to a container comprising reaction fluid such that a quantity of fluid at the end of the duct is only taken by the crescent of the fluid surface when the reaction fluid is moved.

It is advantageous if the device comprises a microtiter plate and a control plane with valves. Apart from valves for controlling through-flows, the control plane can also comprise pumps for the actual conveyance of fluid. On the other hand the control plane can also comprise only valves for controlling through-flows, wherein the actual mass conveyance is implemented by external pumps or pressurisation.

Dividing the microtiter plate and the control plane makes it possible to use microreactor arrays that are based on the standard format for microtiter plates. In this way the microtiter plate can be supplemented by a fluidic dosing system. On the other hand a microtiter plate can also itself form part of the fluid system and can be supplemented only by a control plane. It is advantageous if the control plane comprises an electrical circuit.

Furthermore, it is proposed that a fluid plane and a control plane are combined in a modular manner. In this way reuse of the complex control plane is ensured, while the fluid plane can be produced as a sterile single-use product.

The object on which the invention is based is also met by a method for using a microreactor array for feeding and/or discharging fluids in microreactor arrays through one or several fluid ducts that lead to individual microreactors. Providing the fluid ducts makes it possible to individually control or regulate the fluid ducts. Furthermore, the fluid quantities fed or discharged can be introduced into or withdrawn from the volume of the reaction fluid during a mixing process. A continuous shaking process can ensure adequate mass transport and thorough mixing of the reaction partners or of the fluids. In this process the reaction of the reaction partners is not limited by conditions relating to the metabolic process.

One embodiment of the method provides for a quantity of fluid to be kept at the duct and to be taken only when the reaction fluid is moved through the crescent of the fluid surface.

A particular procedure of the method provides for the required fluid quantities in a first step to be placed into a fluid reservoir provided for this purpose by means of conventional dosing methods such as micro- or nanodispensing, and in a subsequent second step for the access ports for dosing to be sealed off so as to be pressure-proof, and for the predosed quantities of fluid to be pushed at overpressure through the membranes and into the microreactors. In a special procedure of the method, until the end of the reaction of the reaction partners, the reaction space in each microreactor is at each point in time closed either by a membrane or a cover and/or by the fluid-filled fluid systems, in order to in this way prevent any uncontrolled infeed or discharge of matter or contamination.

Furthermore, it is proposed that the microreactor array be covered up by a membrane or a cover, and that all the fluids to be fed and discharged be guided through pre-sterilised materials so as to keep the entire reaction procedure sterile or monoseptic.

Furthermore, the fluids to be fed can be kept ready in an indentation, preferably of one of the reaction chambers on the microreactor array, or in some other receiving vessel that is connected to feed lines. The fluids to be fed can also be kept ready in a separate container that is not being shaken as well, and can then be fed to the individual microreactors by way of ducts or tubes.

BRIEF DESCRIPTION OF THE DRAWINGS

In each case the figures diagrammatically show exemplary embodiments of the invention, further inventions and combinations of features according to the invention.

FIG. 2 shows reservoirs that are connected to the reactors of the microreactor array by way of tubes or flexible fluid ducts;

FIG. 3 shows closing off individual or several fluid ducts that lead to a reactor;

FIG. 4 shows that with a clever arrangement of fluid ducts of the fluid plane and of the pneumatically actuated membranes the fluid pressure or gas pressure in a branch of the fluid duct can be increased;

FIG. 8 shows a further variant of the microreactors wherein the fluid to be dosed is presented through an opening in the cover;

FIG. 9 shows the fluid crescent does not extend to the cover;

FIG. 10, in this manner a cover can individually supply the most minute quantities of fluid to any number of microreactors;

FIG. 11, the individual fluid prechambers 11 are filled by capillary action this volume reduction can be implemented by the heating elements shown in FIG. 11A, or by the piezo crystals shown in FIG. 11B.

DETAILED DESCRIPTION

Figure 1:
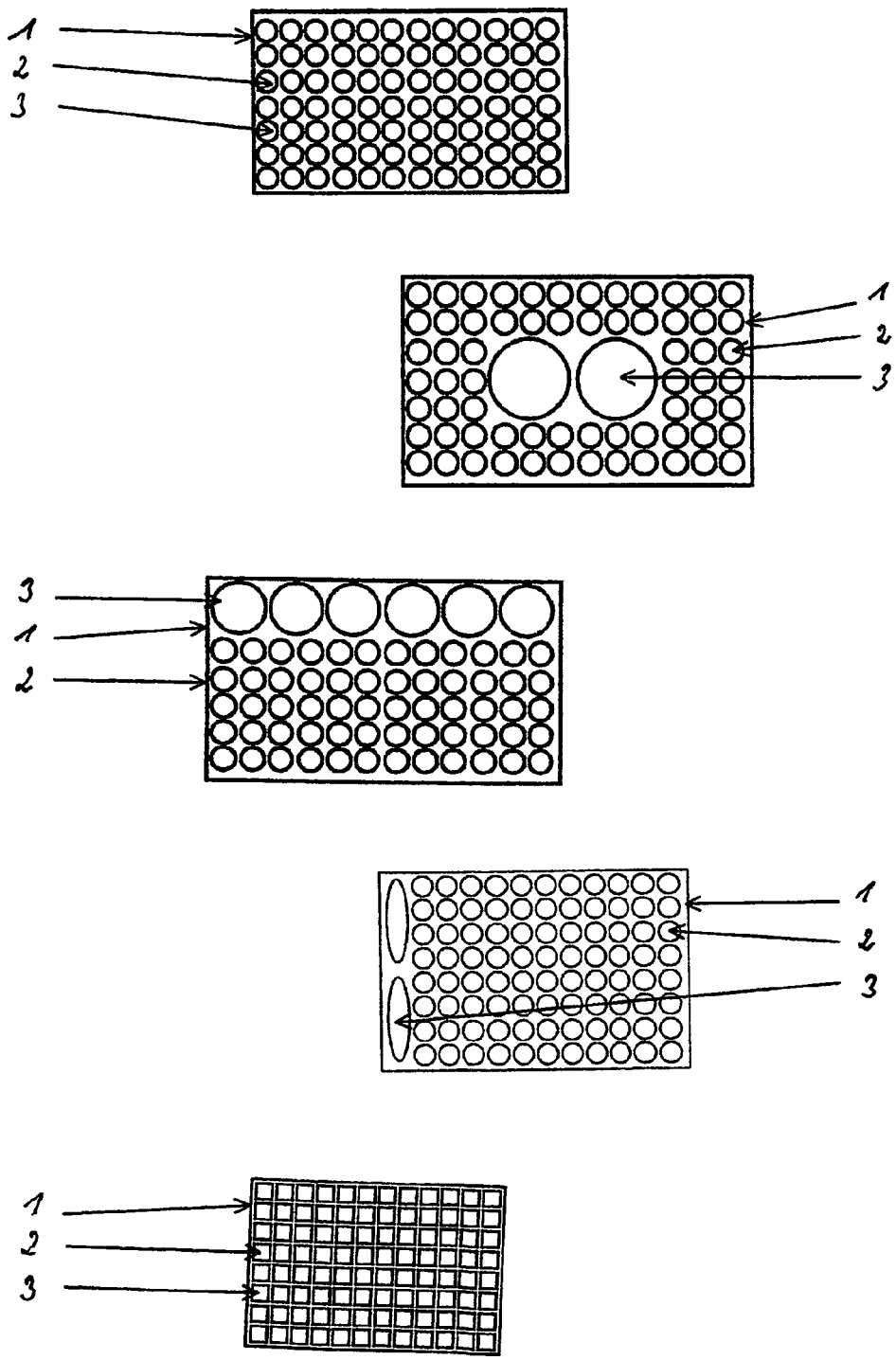
FIG. 1 shows various options of implementing a microreactor array.

FIG. 1 shows various options of implementing a microreactor array 1 that is based on a standard microtiter plate format. In this arrangement it is not mandatory for the geometric arrangements of the individual reactors 2 to be circular. The use of the standardised microtiter plate format ensures unimpeded compatibility with conventional pipetting robots. It is also possible to implement reservoirs 3 on the plate that keep ready the fluids to be fed. Apart from designing the reservoir 3 and the microreactor 2 so that they differ in shape, they can also be identical in shape. For example, in existing microreactor arrays some microreactors 2 can be used as reservoirs 3 for the fluids to be transported. These reservoirs 3 can be implemented on the microtiter plate in any shape and position.

In many cases it may be sensible to keep the fluids that are to be fed to the reactors 2 or that are to be discharged from said reactors 2 ready in separate reservoirs 3 that are not being subjected to shaking. These reservoirs are then connected to the reactors of the microreactor array by way of tubes or flexible fluid ducts 4 as shown in FIG. 2.

Closing off individual or several fluid ducts 4 that lead to a reactor 2 can, as shown in FIG. 3, be implemented by means of thin membranes 8 that are pressurised with compressed air through a pneumatic duct 7, that push into the fluid duct 4 and in this way close off said fluid duct 4. In the example shown, the fluid plane 5 and the pneumatically actuated control plane 6 form part of the bottom of the microreactor array 1. The valves shown in the diagram only have control functions. The actual mass transport can be implemented by external pumping devices.

FIG. 4 shows that with a clever arrangement of fluid ducts 4 of the fluid plane 5 and of the pneumatically actuated 7 membranes 8 the fluid pressure or gas pressure in a branch of the fluid duct 4 can be increased and at the same time further supply ducts can be closed. For example, by way of a single membrane 8 in a single step a duct can be pressurised while other fluid ducts 4 are being closed.

Figure 5:
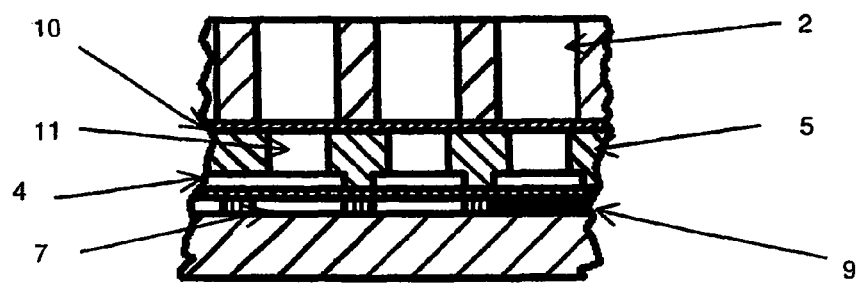
FIG. 5 shows the use of a semi-permeable membrane at the transition from the fluid duct to the reaction chamber.
Figure 6:
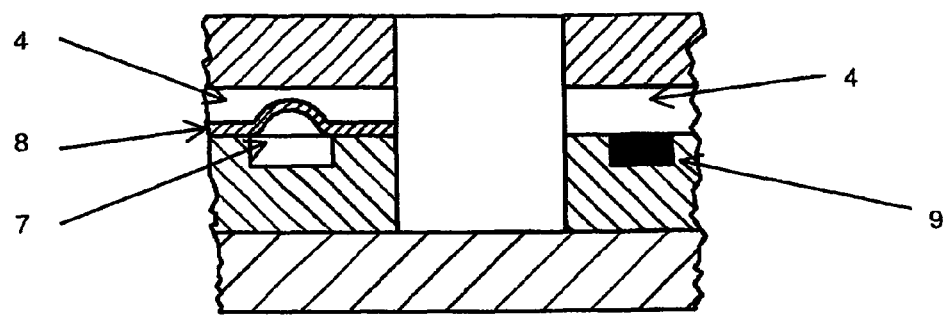
FIG. 6 shows another cross-sectional view.

FIG. 5 shows the use of a semi-permeable membrane 10 at the transition from the fluid duct 4 to the reaction chamber 2. In a simple manner it can minimise any uncontrolled diffuse mass transfer from the duct to the reactor and vice versa. An actuator 9 (e.g. piezo crystal, shape memory alloy, shape-changing polymers, etc.), or a pneumatic duct 7 that is separated by a membrane, provides the pumping capacity required in order to push the medium in the fluid prechamber 11, which medium is to be fed, through the membrane 10 and into the reaction chamber 2.

Figure 7:
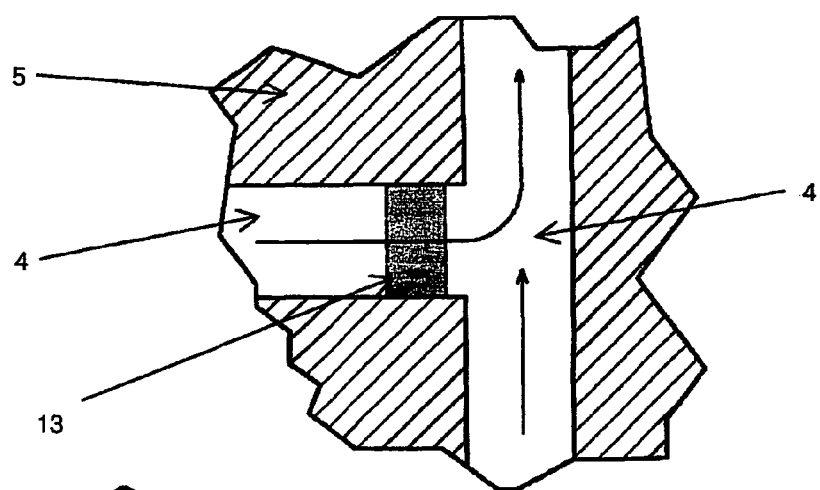
FIG. 7 shows a sidewall feed device.

Apart from the implementation of a duct feed device 4 in the bottom, a sidewall feed device, shown in FIG. 7, can also be sensible. In order to present a droplet on the inside of the reactor 2, so that said droplet is carried along by the crescent generated by shaking, in this arrangement, too, the already mentioned valve techniques or pumping techniques can be used. In this duct arrangement 4, too, the fluid ducts can be controlled by way of pneumatic control ducts or some other actuator arrangement 9 (e.g. shape memory alloys or shape-changing polymers etc.).

Targeted surface treatment of the ducts 4 provides a further option of controlling the fluid flows within the fluid plane. With the transition from hydrophilic to hydrophobic surfaces it is possible to create simple barriers to the fluid flow. In the example shown, such a barrier 13 prevents the fluid from the side duct 4 from flowing into the vertically extending main duct 4. By means of brief pressurisation this barrier 13 can be overcome. Once contact with the main flow has occurred, just a brief interruption of the main flow (e.g. by air bubbles) can again restore the function of the barrier 13. An additional air inlet at the location of the barrier can also cause the inflow from the side duct to cease after a drop in pressure.

In a further variant of the microreactors the fluid to be dosed is presented through an opening in the cover, as shown in FIG. 8. Apart from the fluid ducts 4 through which the fluid is conveyed to the individual reactors 2, the cover also comprises aeration inlets with special membrane inserts 15 in order to ensure sterile gas supply if this is required for the process. To ensure that the droplet presented by the duct 4 can also be taken up in small quantities by the fluid, the fluid crescent 12 generated as a result of shaking needs to extend right up to the fluid duct inlet.

In the case, shown in FIG. 9, where the fluid crescent 12 does not extend to the cover, the droplets detached from the fluid duct 4 need to be accelerated considerably so that the volume of the droplets is kept as small as possible. This approach circumvents the above-mentioned disadvantages of contactless dosing methods. In this embodiment the dosing unit forms part of the cover and can be shaken along with the microreactor array. For this reason, too, the cover needs to comprise fluid ducts 4 and aeration inlets 15 to the individual reactors.

As shown in FIG. 10, in this manner a cover can individually supply the most minute quantities of fluid to any number of microreactors. As shown in FIG. 11, the individual fluid prechambers 11 are filled by capillary action. Due to the very small opening to the reaction chamber 2, no droplets detach as a result of surface tension. It is only as a result of fast actuation that reduces the volume of the fluid prechamber 11 that minute droplets are shot into the reaction chamber. This volume reduction can be implemented by the heating elements 16 shown in FIG. 11A, or by the piezo crystals 17 shown in FIG. 11B.

Figure 12:
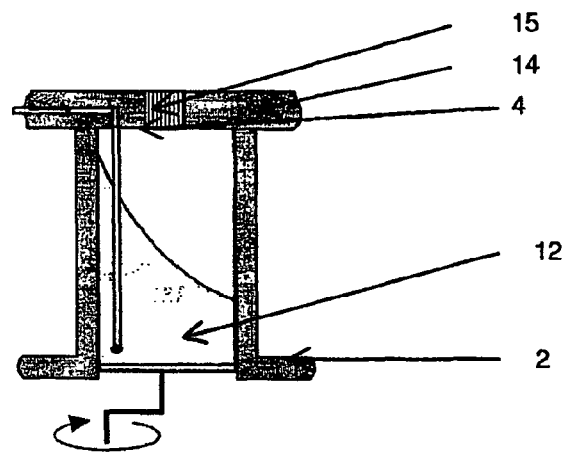
FIG. 12 shows a duct extension to protruding from the cover into the fluid within the reactor where, as shown it is in permanent contact with the fluid.

Instead of the use of highly accelerated droplets for dosing minute quantities of fluid, it is also possible for a duct extension to protrude from the cover into the fluid 12 within the reactor 2, where, as shown in FIG. 12, in permanent contact with the fluid 12, said duct extension ensures the feed or discharge of further media. Any unwanted diffusion into the fluid duct 4 or out of it can to a very large extent be minimised by a very small opening or by a semi-permeable membrane.

Figure 13:
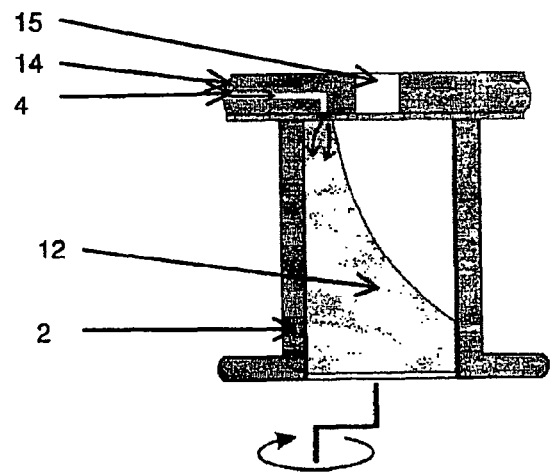
FIG. 13 shows a semi-permeable membrane affixed to the underside of the cover, can be used.

A semi-permeable membrane 10, affixed to the underside of the cover, can be used twofold. As shown in FIG. 13, on the one hand said semi-permeable membrane 10 ensures sterile oxygen exchange at the aeration inlets 15, and on the other hand it enables better control of the fluid infeed through the fluid duct 4. Said semi-permeable membrane 10 prevents diffuse thorough mixing in the fluid duct 4 and allows fluids to pass only if the duct is slightly pressurised.

Figure 14:
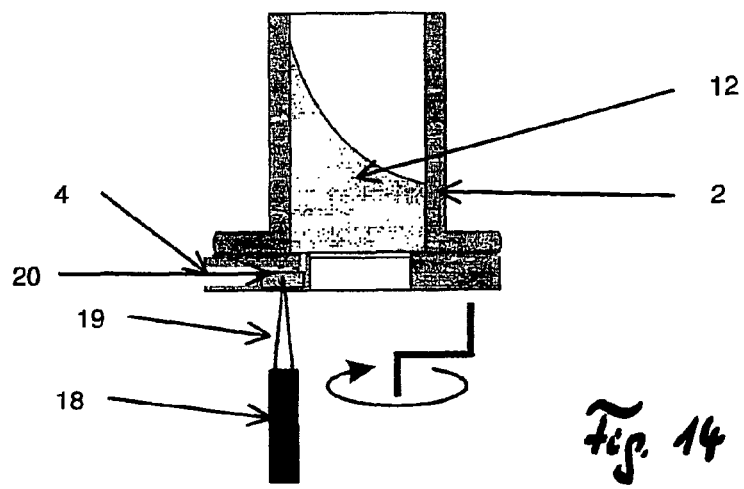
FIG. 14 shows an arrangement in which the microreactor array with its individual reactors is decoupled from the laser light source.

Many materials such as solid polymers or encapsulated polymer gels or metal alloys, which can be used for actuation, in other words as a pump or valve, can be influenced and controlled 20 by electromagnetic waves such as laser light. The example shown in FIG. 14 describes an arrangement in which the microreactor array 1 with its individual reactors 2 is decoupled from the laser light source 18. The microreactor array 1 is shaken, while the stationary laser 18 is focused on a particular point. In order to activate, by means of light, the region to be actuated, either the shaking radius can be selected to be sufficiently small so that the targeted region is never entirely out of focus, or that during the shaking movement said shaking radius is always guided by the laser focus 19. While in this way it is not possible to implement continuous radiation, in most cases, however, pulsed energy input is quite sufficient in order to achieve the desired effects.

Figure 15A:
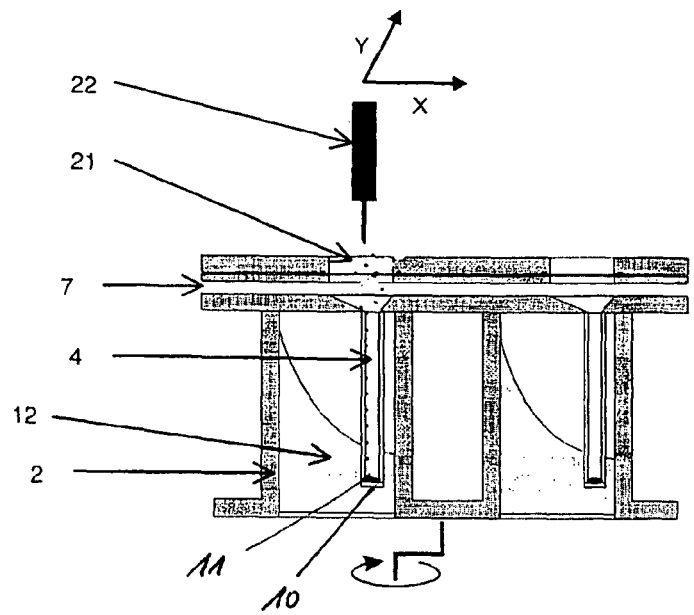
FIG. 15 A shows how in a first step the respectively required quantity of fluid is filled into the corresponding fluid prechambers by means of a micro- or nanodispenser
FIG. 15B shows how the dosing openings 21 are closed after the filling procedure, with pressure is applied to the fluid ducts and the fluid prechambers by way of a pneumatic system.
Figure 15:
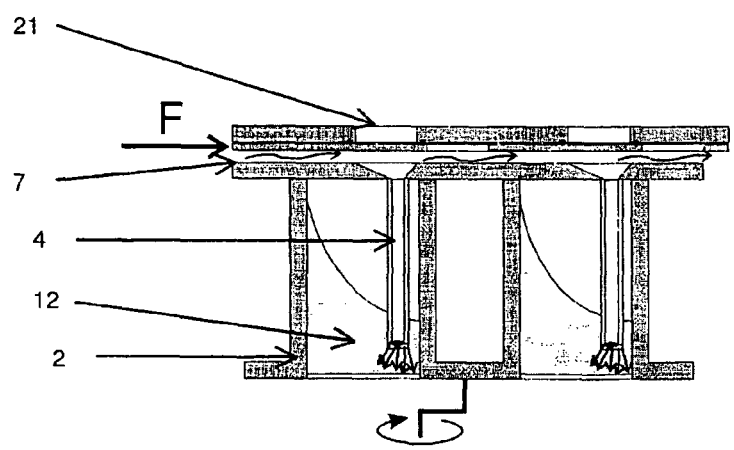

Another approach consists of implementing the dosing and infeed of fluids to the individual reactors 2 in two steps that are independent of each other. FIG. 15A shows how in a first step the respectively required quantity of fluid is filled into the corresponding fluid prechambers 11 by means of a micro- or nanodispenser 22 (e.g. pipetting robot) that travels in the x-y plane. In this arrangement the dosing openings 21 should be selected to be large enough so that the dispenser as a stationary dosing unit 22 need not retrace the shaking movement of the microreactor array 1. By means of a mechanism the dosing openings 21 are closed after the filling procedure, and, as shown in FIG. 15B, pressure is applied to the fluid ducts 4 and the fluid prechambers 11 by way of a pneumatic system 7. This pressure ensures fluid transfer through a semi-permeable membrane 10. The membrane 10 (pore size <0.2 μm) ensures sterile fluid feed.

Figure 16:
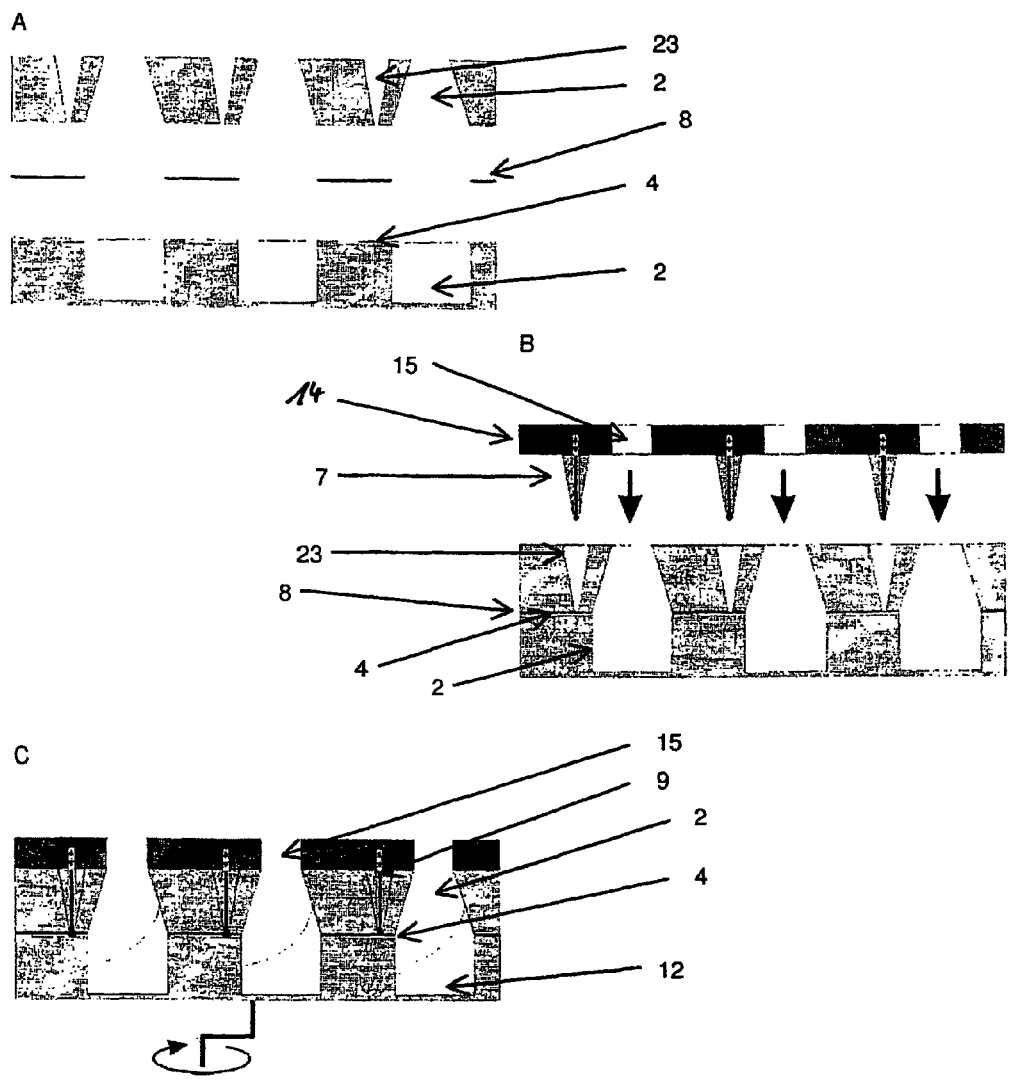
FIG. 16A shows a fluid- and reactor plane comprises three components: a bottom with the reactor chambers and the fluid ducts.
FIG. 16B shows these access ports, are used in order to connect to the membrane the actuator arrangement that is affixed to a cover.
FIG. 16C shows this droplet is sheared off from the fluid crescent.

For commercial application a system is advantageous in which the sterile fluid ducts 4 and the actuators are implemented in systems that are separate of each other. The advantage stems from the re-usability of the expensive actuator arrangement, while the fluid ducts and the reactors can be used as sterile single-use or disposable products. The design, shown in FIG. 16A, of the fluid- and reactor plane comprises three components: a bottom with the reactor chambers 2 and the fluid ducts 4; a thin flexible membrane 8 with recesses at the positions of the reactors 2; and a top fixture that comprises direct access ports to the reactors 2 in order to fill them and in order to ensure the supply of oxygen during the experiments. In addition, the top fixture also comprises access ports 23 to the membrane 8 above the fluid ducts 4. These access ports 23, shown in FIG. 16B, are used in order to connect to the membrane the actuator arrangement 9 that is affixed to a cover 14. Simple self-adjustment of the cover 14 is ensured by means of conical access ports. The actuator arrangement situated in the cover makes it possible to press the membrane into the fluid duct 4 situated underneath it, thus closing off said fluid duct 4. The fluid system 4 first fills itself by capillary action, and after the access ports to the individual reactors 2 have been closed, is pressurised. This pressure can be generated in the cover itself, or it can be generated by external pumps. As a result of a brief opening action of the fluid ducts 4, a small droplet arises on the reactor wall. This droplet is sheared off from the fluid crescent 12 shown in FIG. 16C and is taken along.

Figure 17:
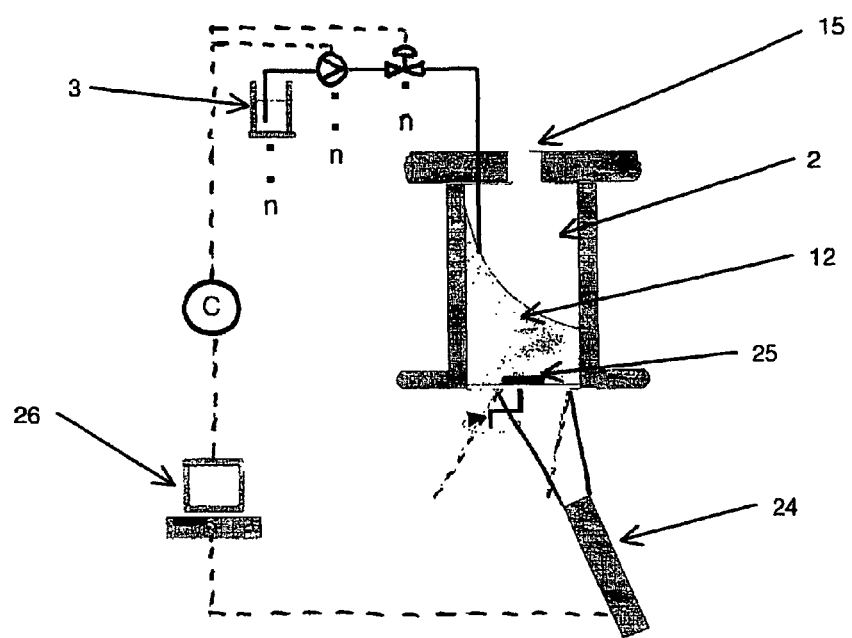
FIG. 17 diagrammatically shows a regulating principle which would, for example, be suitable for a pH-controlled procedure of the analysis.

FIG. 17 diagrammatically shows a regulating principle which would, for example, be suitable for a pH-controlled procedure of the analysis. The pH value in the shaken reactors 2 can be read individually from the outside in a non-invasive manner with the use of optical measuring methods 24. To this effect so-called optodes 25 can be used. The measured value can be acquired and evaluated continuously. By way of a control circuit, the infeed of corresponding adjusters is then controlled. Such a solution can be implemented equally for a substrate—or for some other substance-infeed and fluid discharge. In this case all the process parameters (e.g. pO2, pCO2, T, biomass concentration, etc.), which process parameters have been acquired optically or electrically from the reaction system, can be used as control variables, or as an alternative, the fluids to be fed or discharged are fed or discharged according to a predetermined profile, or as a single pulse or as repeated pulses.

Figure 18:
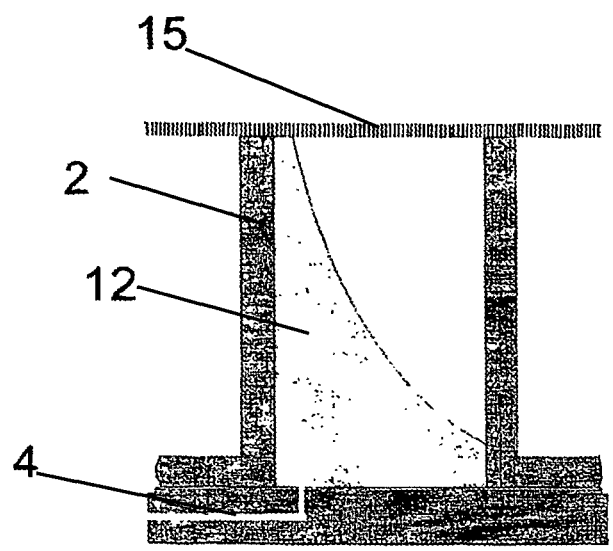
FIG. 18 illustrates one embodiment of the design, wherein the fluid to be dosed is presented through an opening in the reactor bottom.

FIG. 18 again illustrates the primary design of the invention. The fluid to be dosed is presented through an opening in the reactor bottom. A plane underneath the reactor bottom comprises the fluid ducts 4 through which the fluids are conveyed to the individual reactors 2. A gas-permeable membrane 15 can ensure sterile gas infeed to the reactors. The droplets presented through the fluid ducts are taken up into the fluid by the fluid crescent 12 generated by the shaking movement.

Figure 19:
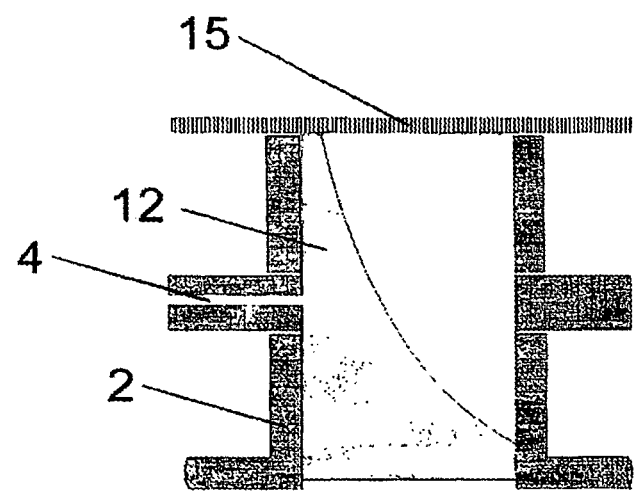
FIG. 19 shows the fluid to be dosed is presented through an opening at half the reactor height

In the variant of the microreactors, which variant is shown in FIG. 19, the fluid to be dosed is presented through an opening at half the reactor height. A mid-plane comprises the fluid ducts 4 through which the fluids are conveyed to the individual reactors 2. A gas-permeable membrane 15 can ensure sterile gas infeed to the reactors. The droplets presented through the fluid ducts are taken up into the fluid by the fluid crescent 12 generated by the shaking movement.

| | List of reference characters |
|---|---|
| 1 | Microreactor array |
| 2 | Microreactor |
| 3 | Reservoir for fluids to be fed or discharged |
| 4 | Fluid duct/tube connection |
| 5 | Fluid plane |
| 6 | Control plane |
| 7 | Pneumatically controlled duct |
| 8 | Flexible membrane |
| 9 | Actuator of any design |
| 10 | Semi-permeable membrane |
| 11 | Fluid prechamber |
| 12 | Fluid crescent |
| 13 | Modified surface |
| 14 | Cover of the microreactor |
| 15 | Aeration inlet to the reactor |
| 16 | Heating elements |
| 17 | Piezo element |
| 18 | Laser |
| 19 | Focused laser beam |
| 20 | Electromagnetically or thermally actuated material |
| 21 | Dosing opening |
| 22 | Dosing unit/pipetting robot |
| 23 | Adjustment openings |
| 24 | Optical reading unit |
| 25 | Optode (varies its fluorescence characteristics depending on chemical variables, e.g. pH value) |
| 26 | Control unit/computer |

The invention claimed is:

1. A device comprising:
a mechanical shaker;
a microreactor array that comprises several containers; and
a gas permeable membrane or lid forming a cover for said containers, wherein said containers are filled partly with liquid and partly with gas;
wherein each container of the array comprises at least one duct that in each case forms a fluid line to the container and comprises at least one acting valve disposed in said microreactor array that makes possible individual feeding of reaction fluids to the individual containers of the microreactor array, wherein said at least one acting valve is configured to be moved by the mechanical shaker which is configured to move the microreactor array; and
wherein the device is configured to operate the mechanical shaker and the at least one duct and the at least one acting valve at least partially simultaneously so that the feeding occurs continuously even during shaking by the mechanical shaker;
a pump, wherein said pump is integrated in the microreactor array.

2. The device according to claim 1, wherein the containers are arranged in one plane, and the duct is arranged below the plane of the containers.

3. The device according to claim 1, wherein the transition between the duct and the container is arranged above the fill plane of the container.

4. The device according to claim 1, wherein said at least one duct is arranged in said cover, said cover having a feed line with an actuatable valve.

5. The device according to claim 1, wherein the array comprises a pump.

6. The device according to claim 1, wherein the array comprises a valve or a pump which is controlled by a focused light beam.

7. The device according to claim 1, wherein the duct comprises a wall as a valve or pump, which wall is deformable by pressure.

8. The device according to claim 1, wherein indentations on the array are designed as pneumatic connections.

9. The device according to claim 1, wherein a partially permeable membrane is arranged in the duct or in the container, the partially permeable membrane being liquid-permeable and gas-permeable.

10. The device according to claim 1, wherein at least one surface of the array is designed to provide optical access.

11. The device according to claim 1, wherein the array comprises sensors, in the individual containers, for the acquisition of data.

12. The device according to claim 11, wherein at least one sensor of the sensors comprises a device for determining pH of a fluid in a container.

13. The device according to claim 1, wherein the shaker acts together with at least one pump that is integrated in the microreactor array to control fluid delivery and mixing.

14. The device according to claim 1, further comprising a microtiter plate and a control plane with valves.

15. The device according to claim 1, wherein a fluid plane and a control plane are combined and are separable again in a modular manner.

16. The device according to claim 1, wherein the fluids to be fed are kept ready on the microreactor array in an indentation.

17. The device according to claim 1, wherein the ducts of the at least one duct are individually controlled and regulated.

18. The device according to claim 1, wherein said at least one valve is disposed in said at least one duct on said microreactor array.

19. The device according to claim 1, wherein said at least one valve is disposed in said cover of said microreactor array.

20. The device according to claim 1, wherein said at least one valve is disposed in said duct, and in said cover of said microreactor array.

21. The device according to claim 1, further comprising a fluid reservoir integrated in the microreactor array and connected to the several containers to provide liquid or gas to the several containers.

22. A method for reaction, the method comprising steps of:
providing a device with a mechanical shaker and a microreactor array, the microreactor array comprising:
a plurality of containers filled partly with liquid and partly with gas;
at least one gas permeable cover for covering the containers;
a plurality of ducts on the plurality of covered containers, respectively, each duct of the plurality of ducts forming a respective fluid line to a respective covered container of the plurality of covered containers; and
at least one valve disposed in said microreactor array, said valve enabling individual feeding of reaction fluids to the plurality of covered containers;
feeding fluids in the microreactor array through the plurality of ducts to the plurality of gas permeable covered containers, and
moving said containers, and said at least one valve with said mechanical shaker;
wherein a pump is integrated into a microreactor array;
wherein the feeding of the fluids and the moving of said containers with said mechanical shaker are carried out at least partially simultaneously such that the feeding is carried out continuously even during the moving; and
wherein the ducts of the plurality of ducts are individually controlled and regulated.

23. The method according to claim 22, wherein a quantity of fluid is kept ready at an inlet of a duct of the plurality of ducts;
wherein when a reaction fluid does not move, the inlet of the duct is not in contact with the reaction fluid; and
wherein only when the reaction fluid is moved does a crescent of the reaction fluid extend right up to the inlet of the duct so that as a result of the crescent the quantity of fluid is removed by the surface of the reaction fluid.

24. The method according to claim 22, wherein the fluids to be fed are kept ready on the microreactor array in an indentation.

25. The method according to claim 22, wherein the array comprises sensors, in the individual containers, for the acquisition of data.

26. The method according to claim 22, wherein said at least one valve is disposed in said cover of said microreactor array.

* * * * *